(12) United States Patent
    Wang

(10) Patent No.: US 11,241,153 B2
(45) Date of Patent: Feb. 8, 2022

(54) METHOD AND APPARATUS FOR PARALLEL OPTICAL COHERENCE TOMOGRAPHIC FUNDUSCOPE

(71) Applicant: Kevin Wang, Charenton le pont (FR)

(72) Inventor: Kevin Wang, Charenton le pont (FR)

(73) Assignee: Kevin Wang, Charenton le pont (FR)

(*) Notice: Subject to any disclaimer, the term of this patent is extended or adjusted under 35 U.S.C. 154(b) by 257 days.

(21) Appl. No.: 16/689,928

(22) Filed: Nov. 20, 2019

(65) Prior Publication Data

US 2021/0145274 A1 May 20, 2021

(51) Int. Cl.
  *A61B 3/10* (2006.01)
  *A61B 3/15* (2006.01)
  *A61B 3/00* (2006.01)
  *A61B 3/12* (2006.01)

(52) U.S. Cl.
  CPC ............ *A61B 3/102* (2013.01); *A61B 3/0008* (2013.01); *A61B 3/12* (2013.01); *A61B 3/156* (2013.01)

(58) Field of Classification Search
  CPC ....... A61B 3/102; A61B 3/156; A61B 3/0008; A61B 3/12; A61B 3/1225; A61B 3/113
  USPC ........................................................ 351/206
  See application file for complete search history.

(56) References Cited

U.S. PATENT DOCUMENTS

| | | | |
|---|---|---|---|
| 8,427,654 B2* | 4/2013 | Horn | G01N 21/4795 356/497 |
| 9,372,067 B2* | 6/2016 | Straub | G01B 9/0203 |
| 2015/0085294 A1* | 3/2015 | Wang | G01B 9/02068 356/479 |

* cited by examiner

*Primary Examiner* — Mohammed A Hasan
(74) *Attorney, Agent, or Firm* — Dragon Son Law Firm, PC; Jinggao Li, Esq.

(57) ABSTRACT

An apparatus for parallel optical coherence tomographic funduscope includes an illumination arm, a processing unit, and a retina imaging interferometer. The illumination arm includes a light source used for emitting incident lights; the processing unit is used for processing raw images from the retina imaging interferometer to obtain fundus images; and the retina imaging interferometer which includes a sample arm, a reference arm, a detection arm and a blocking unit to block unwanted back reflections from optical elements and eye, is used for acquiring the raw images by a camera in the detection arm. The illumination and the reference arms are located in a first light path and the sample and the detection arms are located in a second light path. The blocking unit include a detection pupil located at the intersection of the first and second light paths to block unwanted back reflections from optical elements and eye.

20 Claims, 18 Drawing Sheets

(a)

(b)         (c)         (d)

METHOD AND APPARATUS FOR PARALLEL OPTICAL COHERENCE TOMOGRAPHIC FUNDUSCOPE

TECHNICAL FIELD

The disclosure relates to the field of ophthalmoscope technology, and more particularly relates to method and apparatus for parallel optical coherence tomographic funduscope.

BACKGROUND

Evaluation with funduscope is essential for an eye examination, which can provide valuable diagnostic information to both ophthalmologists and non-ophthalmologists. With respect to the physical examination, the fundus can also be photographed, which allows for documentation and sharing of the images for telemedicine. However, a traditional fundus image, such as red free, infrared, chromatic, and true color fundus image, cannot provide depth sectioning abilities.

Quantitative assessment of retinal anatomy and morphology and of visual function is a critical fundamental step, to characterize disease phenotype, to monitor disease progression, or to evaluate the response to experimental therapies. A quantitative imaging system suitable for routine in vivo assessment of the retinal microstructure makes it possible to correlate structural changes with clinical fundus appearance in real time and at any desired time point in the eye. Monitoring total disease progression over time in the same eye will significantly reduce experimental variability, increase the sensitivity of the corresponding tests, and avoid artifacts due to histologic preparation. Currently, one suitable noninvasive imaging technique for this application is optical coherence tomography (OCT). Specifically, OCT can provide high-resolution, cross-sectional images of the retinal microstructure. Obtaining OCT images of the retina with time domain OCT (TDOCT), spectrum domain OCT (SDOCT) and swept source OCT (SSOCT) have been demonstrated to be feasible.

Generally, both funduscope and OCT are required to be utilized clinically to diagnose a specific human eye disease such as with fundus image. OCT has increased the sensitivity to detect diabetic macular edema and track progression of treatment from focal/grid laser and anti-VEGF therapies.

It is highly desirable to implement the fundus image and OCT image within a shorter time frame, even to implement the same field of view. The direct comparison of fundus and OCT images acquired for a specific ocular disease clinically will help to provide a better understanding the eye disease. While Optovue provided a diagnose platform combined both fundus camera and OCT together, Topcon has provided a device internally combine fundus camera and OCT together, users can select the B-scan line on the enface fundus image to command the system to acquire the OCT depth sectioning image.

However, acquiring images of the in vivo assessment with OCT has been time consuming and challenging. Due to the eye movement, artifacts error might be generated, which were not able to be completely overcome by increasing the scan speed of the OCT. Further, the OCT light path was not compatible to that of the funduscopes, while the OCT modality need to two-dimensionally scan single point illumination on retina and an image along the line of the z-depth (i.e., a scan line image). In order to obtain an enface OCT image, it is required to clumsily extract 2D enface image from the 3D retina image after the time consuming A, B, and C scans. Furthermore, the extracted 2D depth sectioning enface image will contain much more enormous artificial pixels due to eye movements in long scanning period. A fundus camera will take starring enface retina surface image with area light illumination and with no scanning required. Accordingly, it is difficult to directly compare the fundus image and the OCT image and to precisely register the OCT image with the enface fundus images.

Due to the depth sectioning 2D enface OCT image is even impossible to be extracted by OCT modality, fluorescein angiography (FA) and indocyanine green angiography (ICG) image are used to image the retinal vessels by enface fundus camera, which is harmful to subject's health.

Therefore, a heretofore unaddressed need exists in the art to address the aforementioned deficiencies and inadequacies.

SUMMARY

In view of the shortcomings of the existing technology and the actual requirements, an apparatus for parallel optical coherence tomographic funduscope is provided by the present disclosure to obtain parallel coherence tomographic image. Specifically, the starring depth sectioning full field 2D enface retina image will be captured simultaneously. As a result, artifacts error made by eye motion can be completely overcome, and the fundus image can be provided with depth sectioning information.

To achieve this goal, the present disclosure provides the following technical solutions:

First, the disclosure provides an apparatus for parallel optical coherence tomographic funduscope, including:

an illumination arm, a processing unit, and a retina imaging interferometer, wherein the illumination arm includes a light source used for emitting incident lights;

the processing unit is used for processing raw images from the retina imaging interferometer to obtain fundus images; and the retina imaging interferometer that includes a sample arm, a reference arm, a detection arm and a blocking unit to block unwanted back reflections from optical elements and eye, is used for acquiring the raw images by a camera in the detection arm, based on (i) the interference when a reference light reflected from a reference mirror in the reference arm meets a sample light backscattered from a slice of the retina at a given depth in the sample arm and/or (ii) the sample light backscattered from a slice of the retina at a given depth in the sample arm, wherein the illumination and the reference arms are located in a first light path, the sample and the detection arms are located in a second light path, wherein the first light path and the second light path have at least one intersection, and the blocking unit includes a detection pupil located in the second light path to block unwanted back reflections from optical elements and eye, wherein the detection pupil is conjugated with eye pupil plane.

In one embodiment, the apparatus further includes:

a first means for axially displacing the depth of the slice of the retina to be imaged by the camera.

In one embodiment, the apparatus further includes:

a second means for varying the optical path length of the reference arm to match that of the sample arm.

In one embodiment, the processing unit is used for processing the temporal variants of the raw images to present the sub-cellular motions, vibrations and metabolic intracellular activities in retina.

In one embodiment, the apparatus further includes a third means for modulating the relative optical path difference at scale of the wavelength between the sample and the reference arms, around the retina slice at the given depth of the retina.

In one embodiment, the illumination arm further includes a light filter through which the light with a selected wavelength is incident into the retina imaging interferometer for fundus imaging.

In one embodiment, the illumination arm further includes a light intensity modulator to timely vary the light source power to create pulsed or temporarily continuous varying incident light.

In one embodiment, the illumination arm further includes several light sources to be combined in the light path by a beamsplitter or dichroic filter.

In one embodiment, the light source includes LED, Xenon lamp, or halogen lamp.

In one embodiment, the apparatus adopts bright field illumination or dark field illumination. In one embodiment, the illumination arm further includes an internal fixation target to suppress the influence of eye movement and keep the imaging field stable.

In one embodiment, the apparatus further includes an optical conjugation device, which is used for optically conjugating the retina to the sensitive surface of the camera, wherein the optical conjugation device includes a switchable trial lens to statically correct part of the eye aberrations when the corresponding eye aberrations is out of the dynamic correction range of the funduscope.

In one embodiment, the apparatus further includes an optical conjugation device, which is used for optically conjugating the retina to the sensitive surface of the camera, wherein the optical conjugation device includes a badal system.

In one embodiment, the detection arm includes an internal fixation target for keeping the imaging field stable.

In one embodiment, the detection arm includes several cameras to be combined in the light path by a beamsplitter or dichroic filter.

In one embodiment, the sample arm includes a chin rest to support the head of the subject.

In one embodiment, the optical conjugation device includes an optical magnification changer to vary the field of view.

In one embodiment, the reference arm further includes a removable light blocking unit used to switch off depth sectioning ability of the funduscope.

In one embodiment, the detection arm further includes a light filter through which the light with different wavelength is compared to the incident light to be received by the camera.

In one embodiment, the illumination arm further includes an illumination pupil with adjustable shape. On the one hand, the apparatus of the present disclosure can acquire raw 3D images based on OCT technology and/or 2D images like a traditional fundus. Therefore, the apparatus is a parallel optical coherence tomographic funduscope.

On the other hand, the detection pupil of the blocking unit is located in the second light path and conjugated to eye pupil plane the sample arm or the detection arm at the intersection of the first and second straight lines, by adjusting the shape of detection pupil, the present disclosure can block unwanted back reflections from optical elements and eye. The funduscope of the present disclosure can fully utilize the dynamic scope of the camera in the detection arm.

BRIEF DESCRIPTION OF THE DRAWINGS

The accompanying drawings illustrate one or more embodiments of the present disclosure and, together with the written description, serve to explain the principles of the disclosure. Wherever possible, the same reference numbers are used throughout the drawings to refer to the same or like elements of an embodiment.

DETAILED DESCRIPTION

Figure 1:
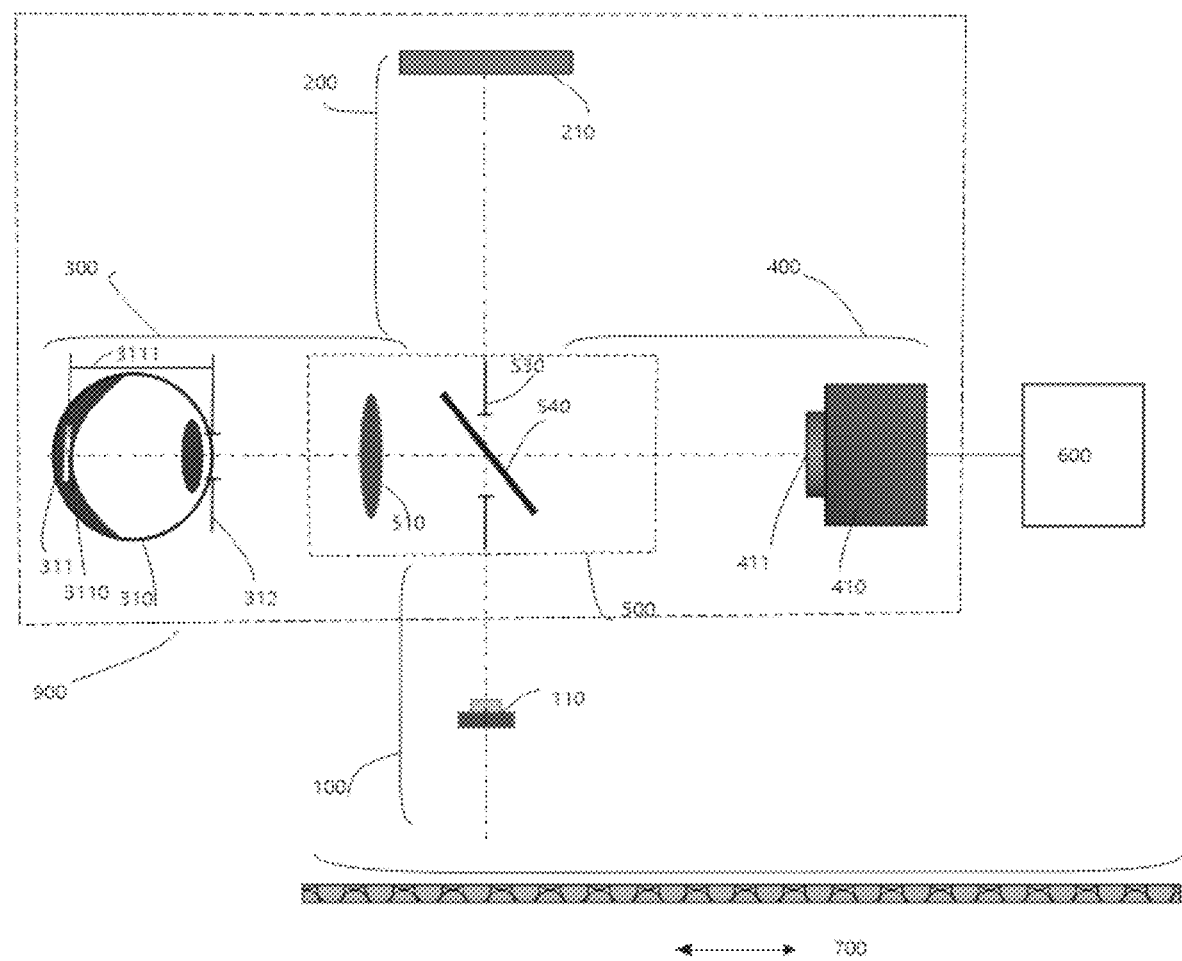
FIG. 1 is a block diagram of an apparatus for parallel optical coherence tomographic funduscope in one embodiment.

The present disclosure will now be described more fully hereinafter with reference to the accompanying drawings, in which exemplary embodiments of the present disclosure are shown. The present disclosure may, however, be embodied in many different forms and should not be construed as limited to the embodiments set forth herein. Rather, these embodiments are provided so that this disclosure is thorough and complete, and will fully convey the scope of the disclosure to those skilled in the art. Like reference numerals refer to like elements throughout.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. For convenience, certain terms may be highlighted, for example using italics and/or quotation marks. The use of highlighting and/or capital letters has no influence on the scope and meaning of a term; the scope and meaning of a term are the same, in the same context, whether or not it is highlighted and/or in capital letters. It is appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only and in no way limits the scope and meaning of the disclosure or of any exemplified term. Likewise, the disclosure is not limited to various embodiments given in this specification.

It is understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It is understood that, although the terms first, second, third, etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below can be termed a second element, component, region, layer or section without departing from the teachings of the present disclosure.

It is understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It is also appreciated by those of skill in the art that references to a structure or feature that is disposed "adjacent" to another feature may have portions that overlap or underlie the adjacent feature.

The terminology used herein is for the purpose of describing particular embodiments only and is not intended to be limiting of the disclosure. As used herein, the singular forms "a", "an", and "the" are intended to include the plural forms as well, unless the context clearly indicates otherwise. It is further understood that the terms "comprises" and/or "comprising," or "includes" and/or "including" or "has" and/or "having" when used in this specification specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top" may be used herein to describe one element's relationship to another element as illustrated in the figures. It is understood that relative terms are intended to encompass different orientations of the device in addition to the orientation shown in the figures. For example, if the device in one of the figures is turned over, elements described as being on the "lower" side of other elements will then be oriented on the "upper" sides of the other elements. The exemplary term "lower" can, therefore, encompass both an orientation of lower and upper, depending on the particular orientation of the figure. Similarly, if the device in one of the figures is turned over, elements described as "below" or "beneath" other elements will then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which the present disclosure belongs. It is further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

As used herein, "around," "about," "substantially" or "approximately" shall generally mean within 20 percent, preferably within 10 percent, and more preferably within 5 percent of a given value or range. Numerical quantities given herein are approximate, meaning that the terms "around," "about," "substantially" or "approximately" can be inferred if not expressly stated.

As used herein, the terms "comprise" or "comprising," "include" or "including," "carry" or "carrying," "has/have" or "having," "contain" or "containing," "involve" or "involving" and the like are to be understood to be open-ended, i.e., to mean including but not limited to.

As used herein, the phrase "at least one of A, B, and C" should be construed to mean a logical (A or B or C), using a non-exclusive logical OR. It should be understood that one or more steps within a method may be executed in different order (or concurrently) without altering the principles of the disclosure.

As used herein, the terms "first", "second", and the like are intended to distinguish different objects rather than describe a specific order or sequence.

Embodiments of the disclosure are illustrated in detail hereinafter with reference to accompanying drawings. It should be understood that specific embodiments described herein are merely intended to explain the disclosure, but not intended to limit the disclosure.

In order to further elaborate the technical means adopted by the present disclosure and its effect, the technical scheme of the present disclosure is further illustrated in connection with the drawings and through specific mode of execution, but the present disclosure is not limited to the scope of the implementation examples.

The disclosure relates to the field of ophthalmoscope technology, and more particularly to an apparatus for parallel optical coherence tomographic funduscope.

In one embodiment, the disclosure provides an apparatus for parallel optical coherence tomographic funduscope, including:

an illumination arm, a processing unit, and a retina imaging interferometer, wherein the illumination arm includes a light source used for emitting incident lights;

the processing unit is used for processing raw images from the retina imaging interferometer to obtain fundus images; and the retina imaging interferometer which includes a sample arm, a reference arm, a detection arm and a blocking unit to block unwanted back reflections from optical elements and eye, is used for acquiring the raw images by a camera in the detection arm, based on (i) the interference when a reference light reflected from a reference mirror in the reference arm meets a sample light backscattered from a slice of the retina at a given depth in the sample arm and/or (ii) the sample light backscattered from a slice of the retina at a given depth in the sample arm, wherein the illumination and the reference arms are located in a first light path, the sample and the detection arms are located in a second light path, wherein the first light path and the second light path have at least one intersection, and the blocking unit includes a detection pupil located in the second light path to block unwanted back reflections from optical elements and eye, wherein the detection pupil is conjugated with eye pupil plane.

For the above-mentioned embodiment, on one hand, because of the above (i) the interference when a reference light reflected from a reference mirror in the reference arm meets a sample light backscattered from a slice of the retina at a given depth in the sample arm, the funduscope of the present disclosure can acquire raw 3D images based on OCT technology. It means that the funduscope can work in depth sectioning mode, being able to create 3D depth sectioning red, blue, green, red free, blood velocity map, capillary perfusion map, metabolic map, and oximetry map images; and/or because of the above (ii) the sample light backscattered from a slice of the retina at a given depth in the sample arm, the funduscope can acquire raw 2D images like a traditional fundus, being able to create enface fundus images, fluorescein angiography (FA), fundus autofluorescence (FAF), and indocyanine green angiography (ICG) images.

On the other hand, because the detection pupil of the blocking unit is located at the intersection of the first and second light paths, the present disclosure can block unwanted back reflections from optical elements and eye. The funduscope of the present disclosure can fully utilize the dynamic scope of the camera in the detection arm.

The funduscope is a novel apparatus for parallel optical coherence tomographic funduscope. The apparatus for parallel optical coherence tomographic funduscope provides staring enface image which can overcome artifacts images due to eye motion by traditional optical coherence tomography (OCT) system, and higher axial and lateral resolution. Combined enface retinal images with depth sectioning information make it much more convenient and powerful for future retina diagnose and research.

It is understood that, the illumination and the reference arms can be located in a first straight line, and the sample and the detection arms can be located in a second straight line perpendicular to the first straight line. In addition, for the illumination arm, the reference arm, the sample arm or the detection arm, each arm can be realized as a more complex optical path rather than a simple linear optical path, provided that the first light path and the second light path have at least one intersection. When there are multiple intersections, this may involve the following more complex situations: (i) the illumination arm crosses the sample arm once; and (ii) the reference arm is led out from a certain position of the sample arm.

As for the detection pupil located in the second light path, it may involve the following situations: (i) the detection pupil is located in the sample arm; and (ii) the detection pupil is located in the detection arm. In addition, for the detection pupil conjugated with eye pupil, i.e., the detection pupil is situated on the plane of eye pupil or the image plane of the eye pupil.

In another embodiment, the funduscope further includes a first means for axially displacing the depth of the slice of the retina to be imaged by the camera.

It is understood that, with the first means, the funduscope can adjust the depth to acquire many 3D and/or 2D retina images at different given depths.

In another embodiment, the funduscope further includes a second means for varying the optical path length of the reference arm to match that of the sample arm.

For the embodiment, the degree of matching is associated with the interference contrast. For example, the optical path of the sample and the reference arms are equal in order to get the best interference contrast.

In one embodiment, the processing unit is used for processing the temporal variants of the raw images to present the sub-cellular motions, vibrations and metabolic intracellular activities in retina. It means that the funduscope can work in the time domain working mode.

In one embodiment, the funduscope further includes a third means for modulating the relative optical path difference at scale of the wavelength between the sample and the reference arms, around the retina slice at the given depth of the retina.

As mentioned above, the retina imaging interferometer allows for the acquisition of more than one raw interferometric image resulting from the interference of a reference light reflected from the reference mirror and the sample light backscattered from the retina. Each raw interferometric image is acquired at a different optical path difference, and the tomographic image is obtained by processing the raw interferometric images with phase shifting algorithm by the processing unit.

Combined with the above, it is understood that, the funduscope can also work in the POCT working mode.

In another embodiment, the illumination arm further includes a light filter through which the light with a selected wavelength incident into the retina imaging interferometer for fundus imaging.

In one embodiment, the illumination arm further includes a light intensity modulator to timely vary the light source power to create pulsed or temporarily continuous varying incident light. It is obvious for one skill in the art that the "pulsed" includes "repeated pulsed".

In one embodiment, the illumination arm further includes several light sources to be combined in the light path by a beamsplitter or dichroic filter.

In one embodiment, the light source includes LED, Xenon lamp, or halogen lamp.

In one embodiment, the apparatus adopts bright field illumination.

Preferably, in bright field illumination scheme, the illumination arm can further include an illumination pupil. Thus, by adjusting the shape of the illumination pupil in illumination arm, only part of the eye pupil will be illuminated. Meanwhile, the shape of the detection pupil in the blocking unit will only collect the back scattered and reflected light from the part of the eye pupil which is the imaging area of the illumination pupil by the retina mirror reflected light. Due to less refractive power of the center area of anterior segment of eye (cornea, pupil, lens etc), illumination on the center area of eye pupil may bring large amount of unwanted back reflections. Therefore, the above detection pupil of the blocking unit will be center obscure to block the unwanted back reflections.

In one embodiment, the funduscope adopts dark field illumination.

Preferably, in dark field illumination scheme, the illumination arm can also include an illumination pupil. Thus, by adjusting the shape of the illumination pupil in illumination arm, only part of the eye pupil will be illuminated. Meanwhile, the shape of the detection pupil will only pass the back scattered light from the part of the eye pupil aside of the imaging area of the illumination pupil by the retina mirror reflected light. For light reflected from retina following the reflection law will be blocked in dark field illumination. Thereafter, the detection pupil of the blocking unit will block the unwanted back reflections from the anterior segment of eye (cornea, pupil, lens etc) and optical elements.

In both bright field and dark field illumination scheme, the above detection pupil is better used to suppress unwanted back reflections by the optical elements and eye in order to fully utilize the dynamic scope of the camera.

It's understood that, in one embodiment, the illumination arm further includes an illumination pupil with adjustable shape. Thus, the above detection pupil is better used to suppress unwanted back reflections by the optical elements and eye in order to fully utilize the dynamic scope of the camera.

In one embodiment, the illumination arm further includes an internal fixation target to suppress the influence of eye movement and keep the imaging field stable.

In order to suppress the influence of the eye movement and keep the imaging field stable, there will be an internal fixation target inserted into the illumination arm. By moving the position of the target off the optical axis, different slice of the retina (i.e., field of view) can be selected at the same depth.

In one embodiment, the funduscope further includes an optical conjugation device, which is used for optically conjugating the retina to the sensitive surface of the camera, wherein the optical conjugation device includes a switchable trial lens to statically correct part of the eye aberrations when the corresponding eye aberrations is out of the dynamic correction range of the funduscope.

It is understood that, for different subject, the eye aberrations may vary. The optical conjugation device, which is for optically conjugating the retina to the camera sensitive surface, needs to compensate at least the low order eye aberrations, such as myopia or hyperopia. When the aberration is out of the system dynamic adjusting range, a switchable trial lens can statically correct part of the eye aberrations, and dynamically eliminate the remainder by adjusting other optical elements.

Referring to FIG. 1, light beam from LED 110 with areal emitting surface in illumination arm 100 enters the retina imaging interferometer 900, and the a beamsplitter 540 separates the incident light into two beams, in which one beam passes through lens 510 and eye pupil 312 and then enters the sample arm 300 to illuminate the retina 311 in the eye 310, and the other beam enters the reference arm 200 to illuminate the reference mirror 210.

The retina imaging interferometer 900 includes the reference arm 200, sample arm 300, optical conjugation device 500 and detection arm 400. The optical conjugation device 500 optically conjugates the slice 3110 of the retina 311 to the sensitive surface 411 of the camera 410 in detection arm 400.

The interferometer 900 allows for the acquisition of images resulting from the interference of the reference wave obtain by the reflection of the incident wave on the reference mirror 210 and the sample wave obtained by backscattering of the incident wave by the slice of the retinal 3110 at the given depth 3111. The detection pupil 530 conjugates to the eye pupil 312 to block unwanted hack reflections from optical elements and the eye 310.

The processing unit 600 is used for processing the raw images to obtain the result retina image.

The linear translation stage 700 axially displaces the optical conjugation device 500 and detection arm 400 for conjugating the retina slice 3110 at different depth 3111 to camera sensitive surface 4110 for 3D image stacks.

In another embodiment, the funduscope further includes an optical conjugation device, which is used for optically conjugating the retina to the sensitive surface of the camera, wherein the optical conjugation device includes a badal system.

During the procedure of imaging, the eye aberration may temporarily vary, in order to re-conjugate the retina slice at a given depth to the camera, and the sample arm length may vary, too. Therefore, the reference arm length needs to be dynamically adjusted to keep the high contrast of the interference pattern. A badal system in the light path can compensate the aberration while keeping the sample arm length constant. As such, there is no need to vary the reference arm length.

In one embodiment, the detection arm includes an internal fixation target to keep the imaging field stable.

It is understood that the internal fixation target can also be inserted into the detection arm for keeping the imaging field stable. By moving the position of the target off the optical axis, different slice of the retina (i.e., field of view) can be selected at the same depth.

In one embodiment, the detection arm includes several cameras to be combined in the light path by a beamsplitter or dichroic filter.

For this embodiment, in order to simultaneously have fundus images at different spectrums, several cameras can be combined into the light path by a beamsplitter or dichroic filter. While with a beamsplitter, part of light energy will get lost. The dichroic filter is another common method to combine light with possible less light energy loss.

In one embodiment, the sample arm includes a chin rest to support the head of the subject.

In order to fix the eye position when imaging, a chin rest can be used to comfortably support the head of the subject. In addition, it is preferred to fix the head with a fasten trip.

In one embodiment, the optical conjugation device includes an optical magnification changer to vary the field of view.

In order to implement different field of view, an optical magnification changer may be included in the optical conjugation device to vary the field of view. It can be a switchable group of lenses (such as Galilien magnification changer) to implement several distinct magnifications, or complex zoom lens to continuously vary the magnification.

In another embodiment, the reference arm further includes a removable light blocking screen used to switch off depth sectioning ability of the funduscope.

It is understood that the above embodiment is for the traditional fundus working mode. In order to compare with traditional fundus image, a removable light blocking screen can be inserted into the reference arm such as a beam absorber. Because the light from the reference arm is eliminated, the apparatus works as a normal traditional fundus camera without depth sectioning, and it could detect red, blue, green, red free, blood velocity map, capillary perfusion map, metabolic map, oximetry map image as the described in published articles and the various fundus cameras in current market.

In one embodiment, the detection arm further includes a light filter through which the light with different wavelength is compared to the incident light to be received by the camera.

While working as a traditional fundus camera, in order to detect fluorescent retina image, such as fluorescein angiography (FA), fund us autofluorescence (FAF), indocyanine green angiography (ICG) image, a light filter through which the fluorescent light passed can be inserted before the camera. The fluorescent light received by the camera is generally with different wavelength to the incident light for exciting the retina.

Figure 2:
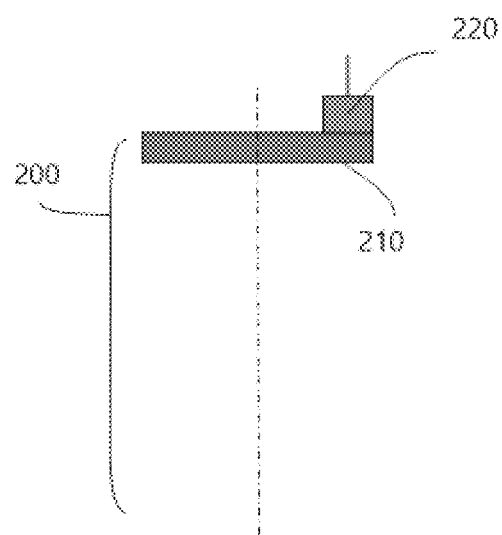
FIG. 2 is an example for a means modulating the relative optical path difference between the sample and the reference arms in another embodiment.

FIG. 2 is an example for a means modulating the relative optical path difference between the sample and the reference arms. A piezoelectric ceramic 220 is installed on reference mirror 210 in reference arm 200 to modulate the relative optical path difference at scale of wavelength.

Around the retina slice 3110 at the given depth 3111, the retina imaging interferometer 900 allows for the acquisition of more than one raw interferometric images resulting from the interference of a reference wave reflected from the reference mirror 210 and the sample wave backscattered from the retina slice 3110.

Each raw interferometric image is acquired at different optical path difference, and the tomographic image is obtained by processing the raw interferometric images with phase shifting algorithm by the processing unit 600.

Figure 3:
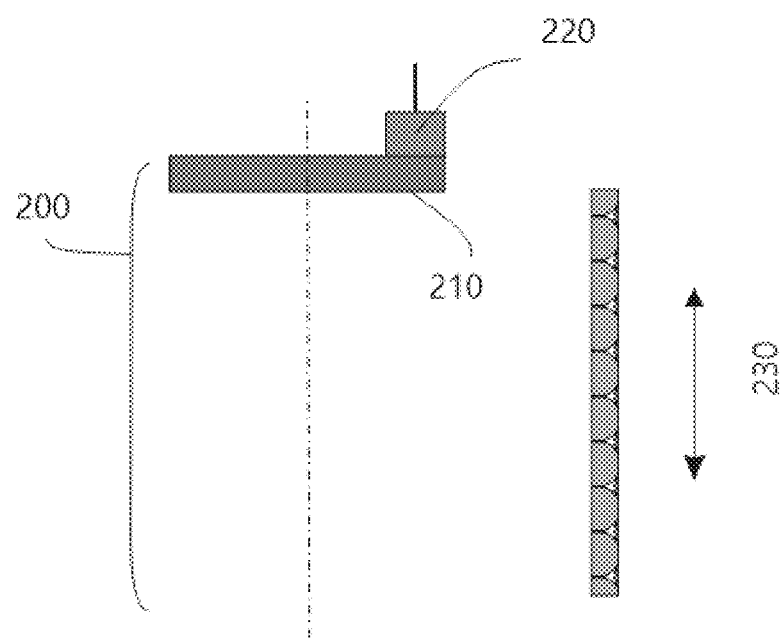
FIG. 3 is an example for a means varying the relative optical path the reference arm to match the focal plane of the sample arm in one embodiment.

FIG. 3 is an example for a means varying the relative optical path the reference arm 200 to match the arm length of the sample arm 300. The linear translation stage 230 in the reference arm 200 varies its optical path length to match the arm length of the sample arm, i.e., the optical path of the sample and the reference arms to be equal in order to get the best interference contrast.

Figure 4:
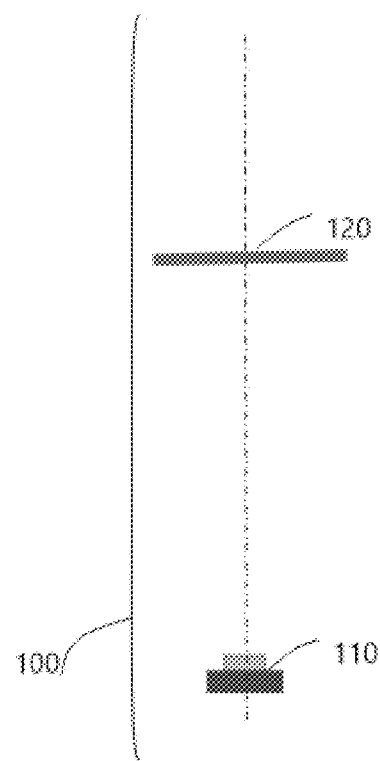
FIG. 4 is an illumination arm with an inserted light filter in another embodiment.

FIG. 4 is an illumination arm 100 with a light filter 120 inserted. The light filter 120 is arranged in the illumination arm 100, and only part of the incident light with specific wavelength is used for imaging. It could create depth sectioning red, green, blue, red free, and infrared image, and to analyze the blood velocity map, capillary perfusion map, metabolic map, and oximetry map image.

Figure 5:
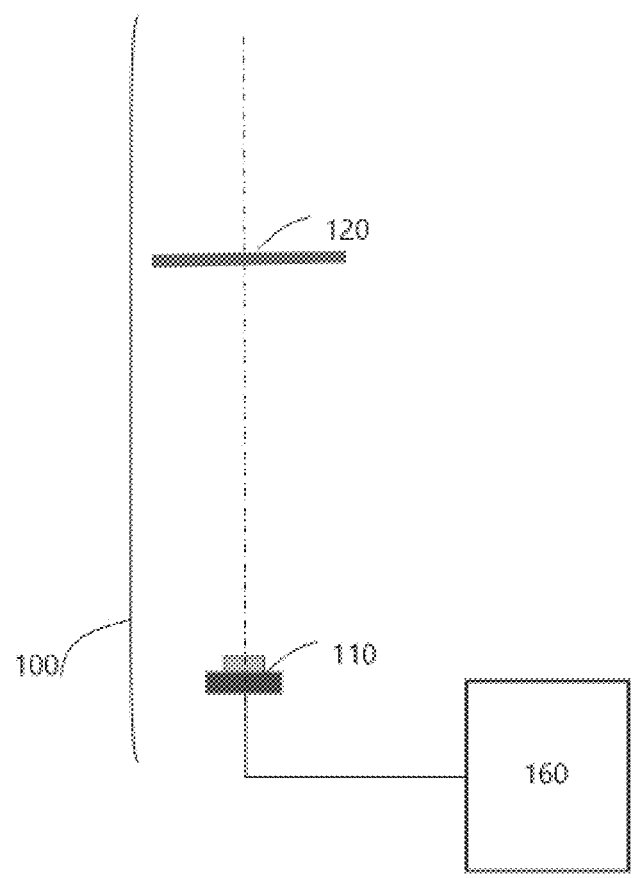
FIG. 5 is an illumination arm with a light intensity modulator to timely vary the light source power in another embodiment.

FIG. 5 is an illumination arm with a light intensity modulator 160 to timely vary the electric power of the light source 110. The modulator 160 varies the light intensity of the light source 110 in illumination arm 100. For visible illumination, the flash light is preferable to the continuous light so that the intensity for camera exposure can increased to get better signal to noise ratio within eye safe limitation. By modulating with single pulse or periodically modulating the power of the visible incident light, with the images by invisible infrared light the apparatus can be used to analyze the intrinsic optical signal image for further retina function imaging.

Figure 6:
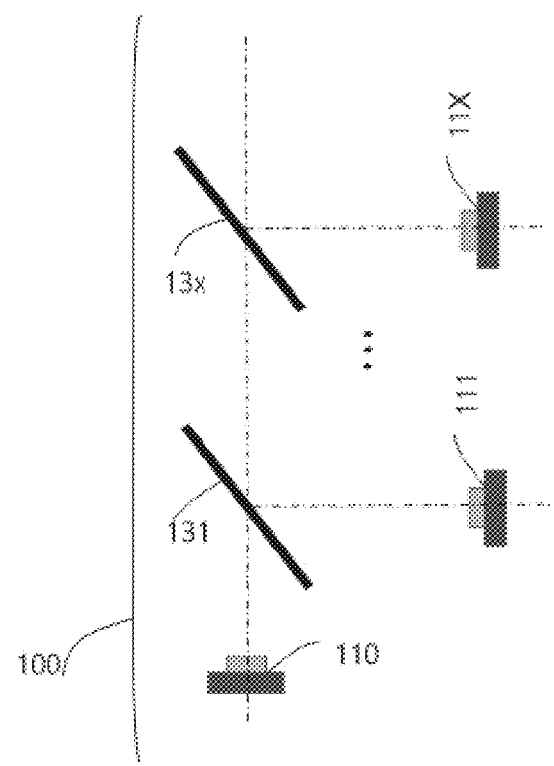
FIG. 6 is an illumination arm with several light sources combined into the light path by a beamsplitter or dichroic filter in another embodiment.

FIG. 6 is an illumination arm 100 with several light sources combined into the light path by a beamsplitter or dichroic filter. For the incident light with a specific spectrum, extra light source 111 can be merged into the illumination arm 100 by a beamsplitter 131, and light source 11x can be merged into the illumination arm 100 by a dichroic filter 13x. While with the a beamsplitter 131, part of light energy will get lost, the dichroic filter 13x will possibly make less light energy loss.

Figure 7:
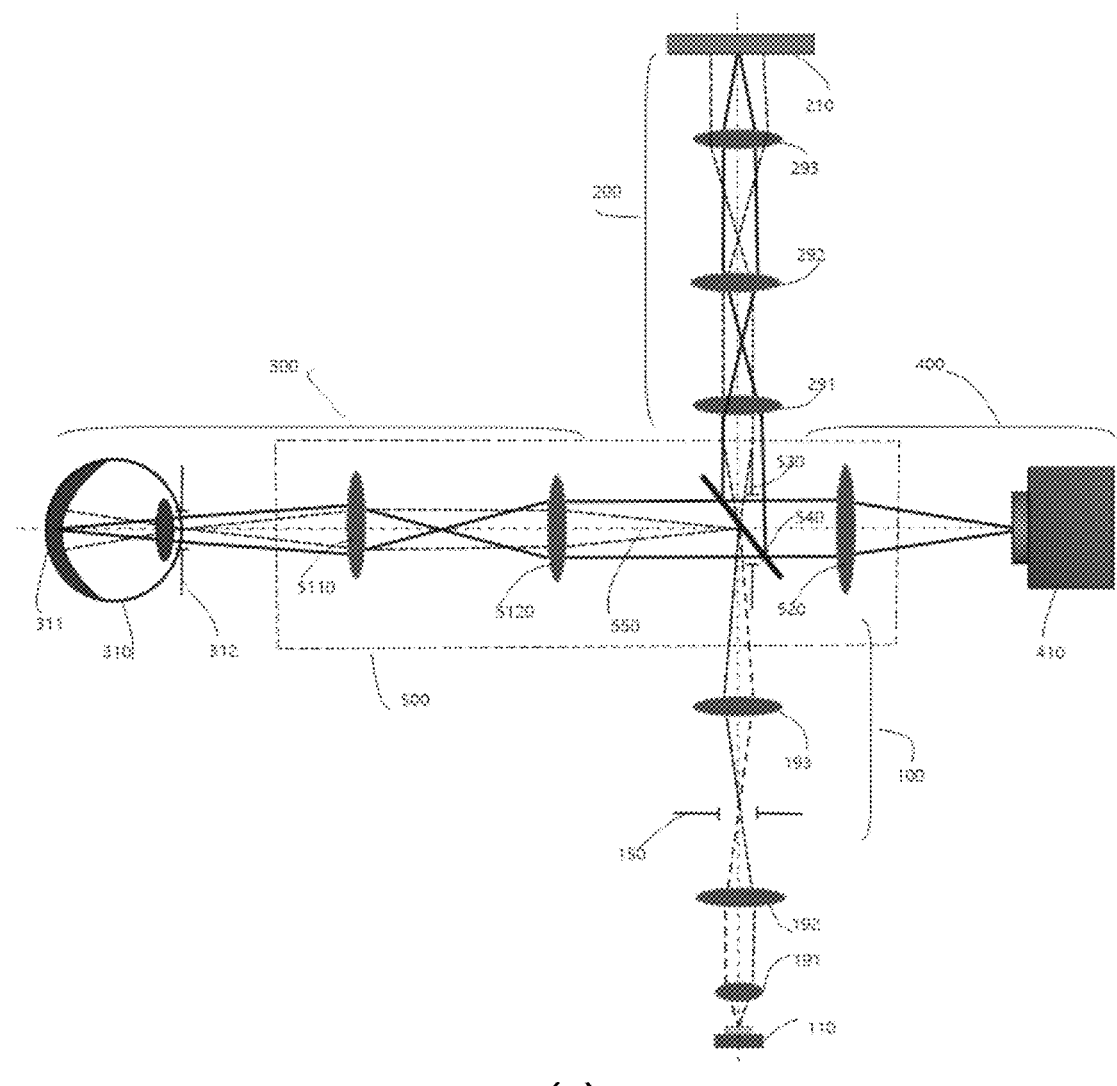
FIG. 7 is an example for dark field illumination in another embodiment.
Figure 7:
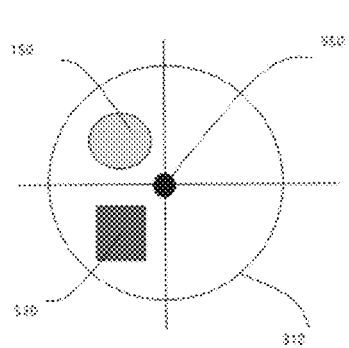
Figure 7:
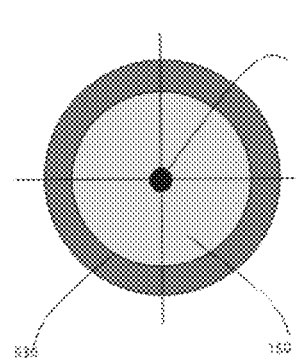
Figure 7:
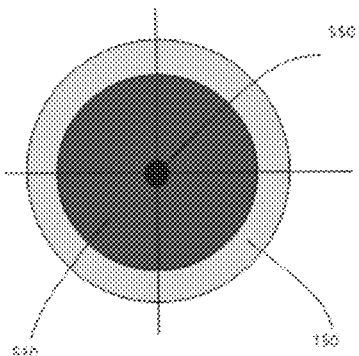

FIG. 7 is an example for dark field illumination:

(a) a scheme of dark illumination.

The light beam from LED 110 with areal emitting surface in illumination arm 100 is collimated by lens 191 and relayed onto the a beamsplitter 540 by lens 192, and lens 193. The a beamsplitter 540 separates the incident light into two beams: one beam passes through the lens 5120, lens 5110, eye pupil 312 in sample arm 300 to illuminate the retina 311 in eye 310, and the other beam passes through lens 291, lens 292, and lens 293 to illuminate the reference mirror 210 in the reference arm 200. The illumination pupil 150, the detection pupil 530 and the eye pupil 312 are conjugated. On the plane of the blocking unit, the detection pupil 530 is arranged, the image of the illumination pupil 150 by reflected light from eye and detection pupil 530 are not overlapped and only take part of the image of the eye pupil 312 scheme. The detection pupil can be a physical screen, or the conjugated image of a physical screen arranged in sample arm, or a plane formed by several conjugated images of physical screens arranged in sample arm and detection arm individually, or a plane formed by a physical screen situated on detection pupil combined with conjugated images of several physical screens arranged in sample arm and detection arm individually.

(b) the situation where the image of the illumination pupil 150 and the detection pupil 530 is off optical axis 550 and within the image of the eye pupil 312.

(c) the situation where the image of the illumination pupil 150 is circular shape and the detection pupil 530 is annular shape on optical axis 550, and both are within the image of the eye pupil 312.

(d) the situation where the image of the illumination pupil 150 is annular shape and the detection pupil 530 is circular shape on optical axis 550, and both are within the image of the eye pupil 312.

Figure 8:
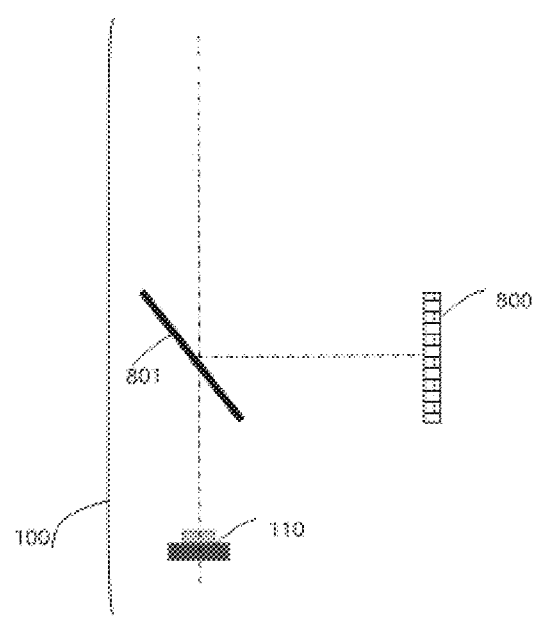
FIG. 8 is an illumination arm with an internal fixation target inserted in another embodiment.

FIG. 8 is an illumination arm 100 with an internal fixation target 800 inserted. The fixation target is combined into the illumination arm 100 with a beamsplitter or dichroic filter 801.

Figure 9:
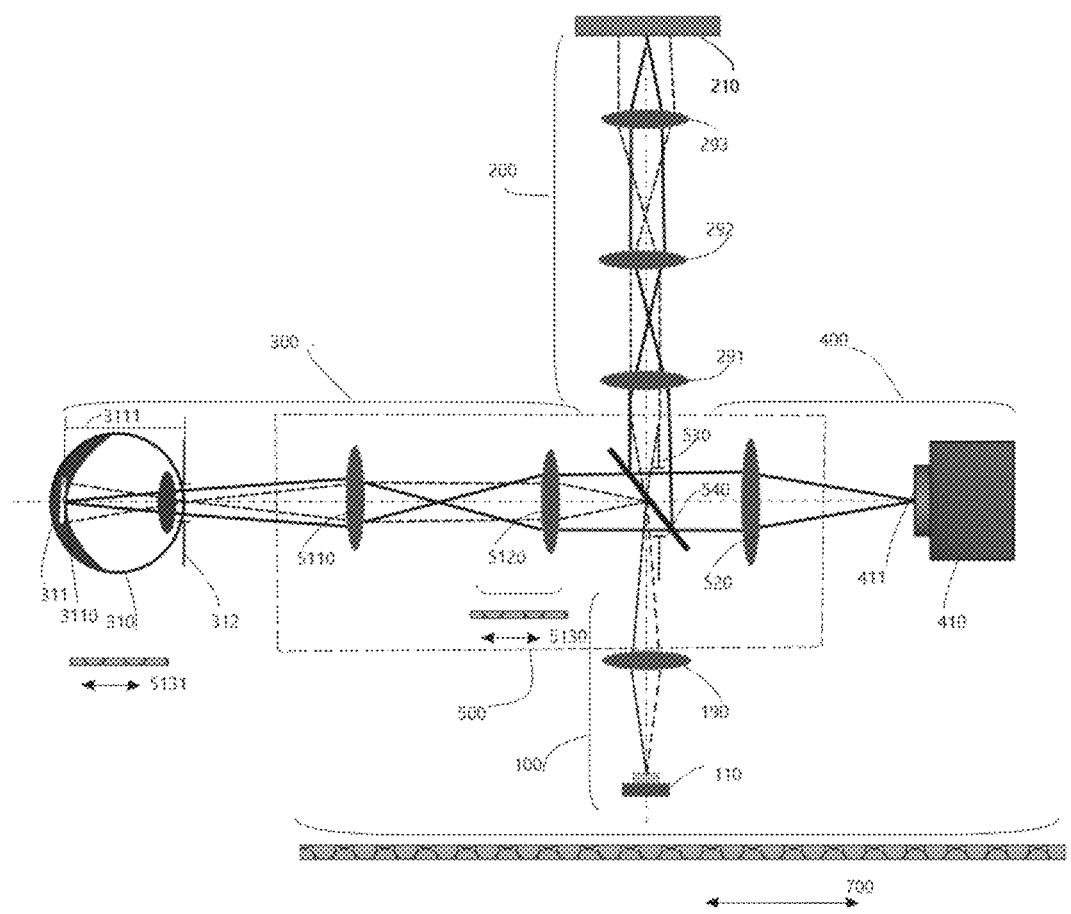
FIG. 9 is an example of the optical conjugation device in another embodiment.

FIG. 9 is an example of the optical conjugation device 500 which dynamically corrects eye defocus by displacing a lens 5110 and the eye 310 axially. Light beam from LED 110 with areal emitting surface in illumination arm 100 is incident on the beam splitter 540, then separated into two beams, in which one beam passes through lens 5120, lens 5110, eye pupil 312 in sample arm 300 to illuminate the retina 311 in eye 310, and the other beam passes through lens 291, lens 292, and lens 293 to illuminate the reference mirror 210 in the reference arm 200. The optical conjugation device 500 optically conjugates the slice 311 of the retina 311 to the sensitive surface 411 of the camera 410 in detection arm 400. When there is defocus aberration caused by the myopia or hyperopia of the eye 310, it is to axially displace the lens 5120 by the linear translation stage 5130 and the eye 310 by the linear translation stage 5131 to obtain the light scattered from the retina slice 3110 collimated after the lens 5120, and hence the retina slice 3110 is conjugated to the camera sensitive surface 4110 at the focal plane of the lens 520 again. Meanwhile, the optical path of the sample arm 300 varies with the movement of the linear translation stage 5130 and 5131, and hence the optical path of the reference arm 200 is required to be varied to match the updated optical path of the sample arm 300. The linear translation stage 700 axially displaces the optical conjugation device 500, reference arm 200 and detection arm 400 for conjugating retina slice 3110 at different depth 3111 to the camera sensitive surface 4110.

Figure 10:
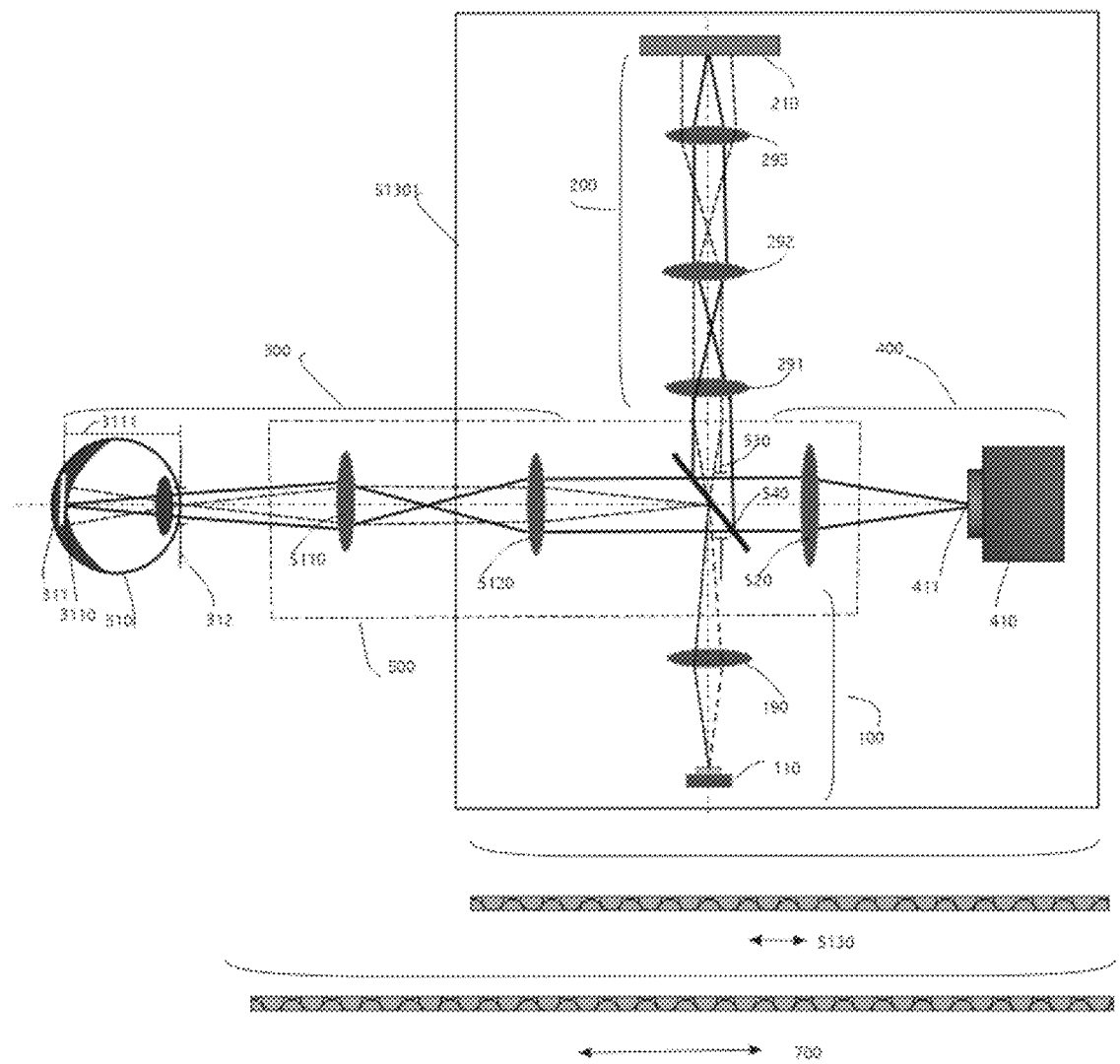
FIG. 10 is an example of the optical conjugation device with a badal system in another embodiment.

FIG. 10 is an example of the optical conjugation device 500 which dynamically corrects eye defocus by a badal system. Light beam from LED 110 with areal emitting surface in illumination arm 100 is incident on the a beamsplitter 540, then separated into two beams, in which one beam passes through lens 5120, leans 5110, eye pupil 312 in sample arm 300 to illuminate the retina 311 in eye 301, and the other beam passes through lens 291, lens 292, lens 293 to illuminate the reference mirror 210 in the reference arm 200. The optical conjugation device 500 optically conjugates the slice 311 of the retina 311 to the sensitive surface 411 of the camera 410 in detection arm 400, wherein lens 5120 in sample arm and lens 530 in detection arm make up a badal system. When there is defocus aberration caused by the myopia or hyperopia of the eye 310, it is to axially displace the badal compensation part 51301, which includes the illumination arm 100, the reference arm 200, the detection arm 400 and part of the sample arm 300, by the linear translation stage 5130, and the retina slice 3110 can be conjugated to the camera sensitive surface 4110 again. Meanwhile, the optical path of the sample arm 300 remains constant with the movement of the linear translation stage 5130. Hence, the optical path of the reference arm 200 is not required to vary to match the updated optical path of the sample arm. The linear translation stage 700 axially displaces the optical conjugation device 500 and detection arm 400 for conjugating retina slice 3110 at different depth 3111 to camera sensitive surface 4110.

Figure 11:
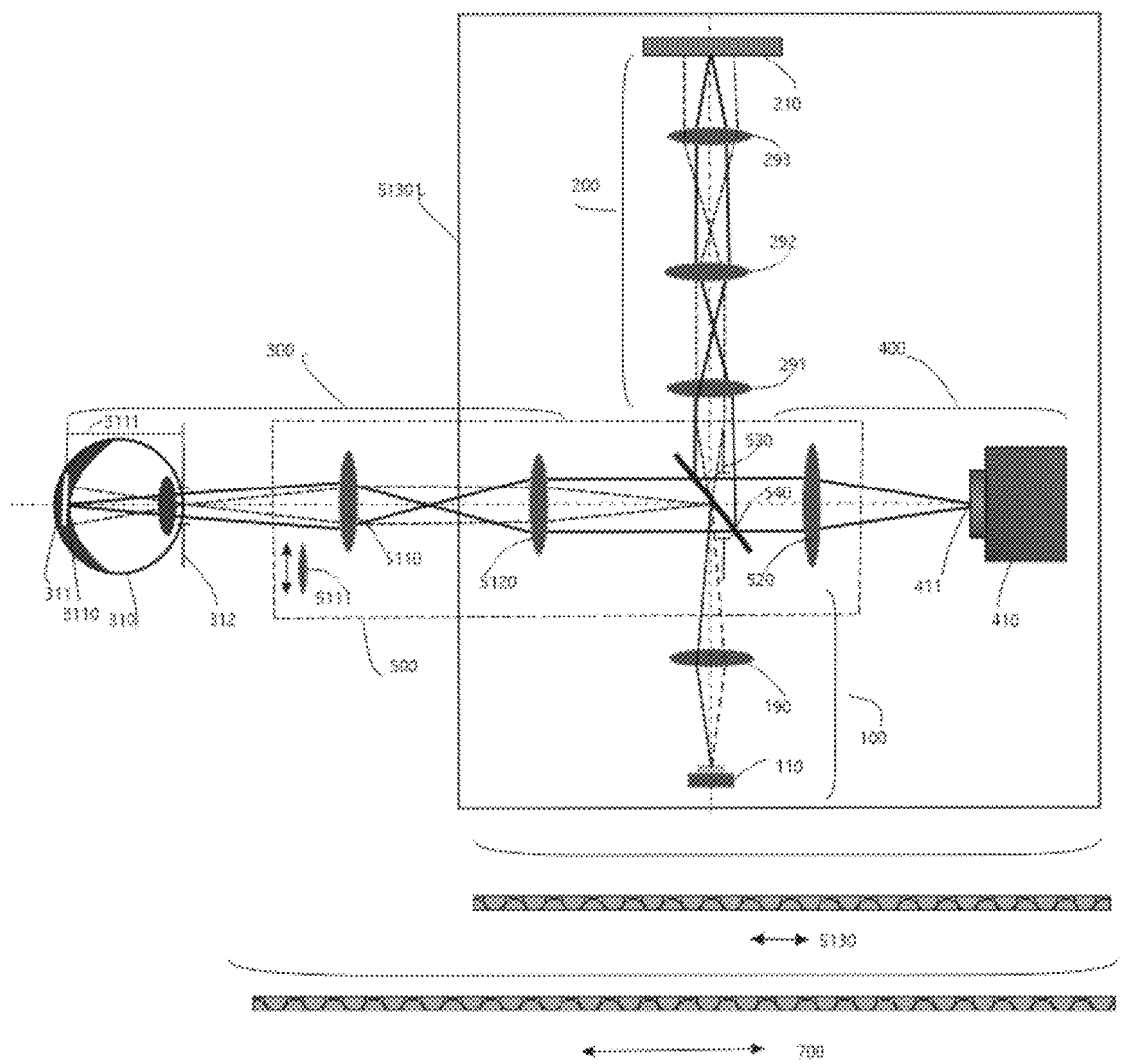
FIG. 11 is an example of the optical conjugation device with trial lens in another embodiment.

FIG. 11 is an example of the optical conjugation device 500 in which the trial lens 5111 is used for correcting static eye aberrations which is out of the system dynamic correction range. The optical layout is the same as FIG. 10 except that there is a trial lens 5111, which can be switchable and inserted into the light path.

Figure 12:
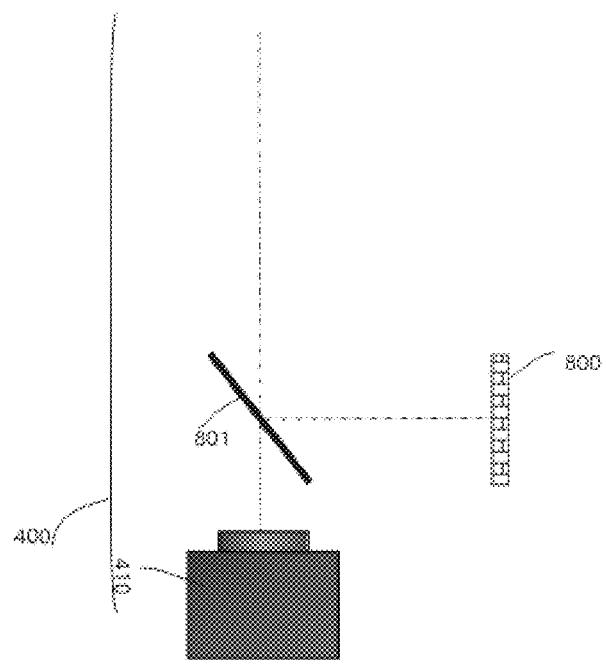
FIG. 12 is a detection arm with an internal fixation target inserted in another embodiment.

FIG. 12 is a detection arm 400 with internal fixation target 800 inserted. The fixation target is combined into the detection arm 100 with a beamsplitter or dichroic filter 801.

Figure 13:
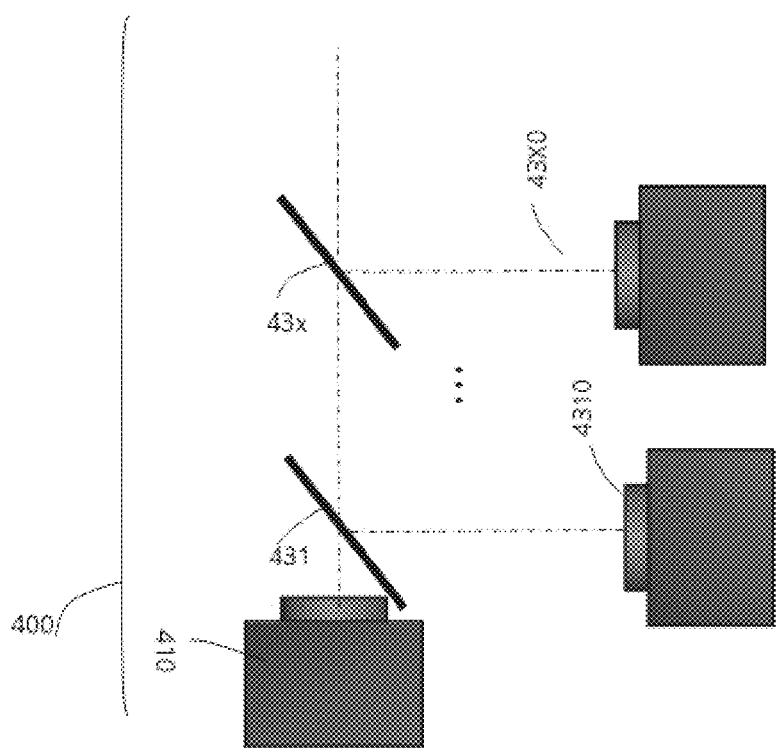
FIG. 13 is a detection arm with several cameras combined into the light path by a beamsplitter or dichroic filter in another embodiment.

FIG. 13 is a detection arm 400 with several cameras combined into the light path by a beamsplitter or dichroic filter. In order to acquire the back scattered light by different cameras (such as color camera and chromatic camera), an extra camera 4310 can be merged into the detection arm 400 by a beamsplitter 431. In order to acquire the back scattered light at different spectrums such as fluorescence light excited from the retina, another extra camera 43X0 can be merged into the detection arm 400 by a dichroic filter 43*x*. While with the a beamsplitter 411, part of light energy will get lost, and the dichroic filter 43*x* will possibly make less light energy loss.

Figure 14:
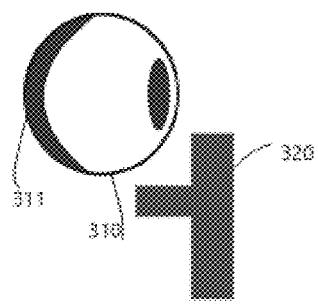
FIG. 14 is a sample arm including a chin rest in another embodiment.

FIG. 14 is a sample arm including a chin rest 320 to support the head of the subject. In order to obtain stable image, a chin rest 320 is used to hold the head of the subject.

Figure 15:
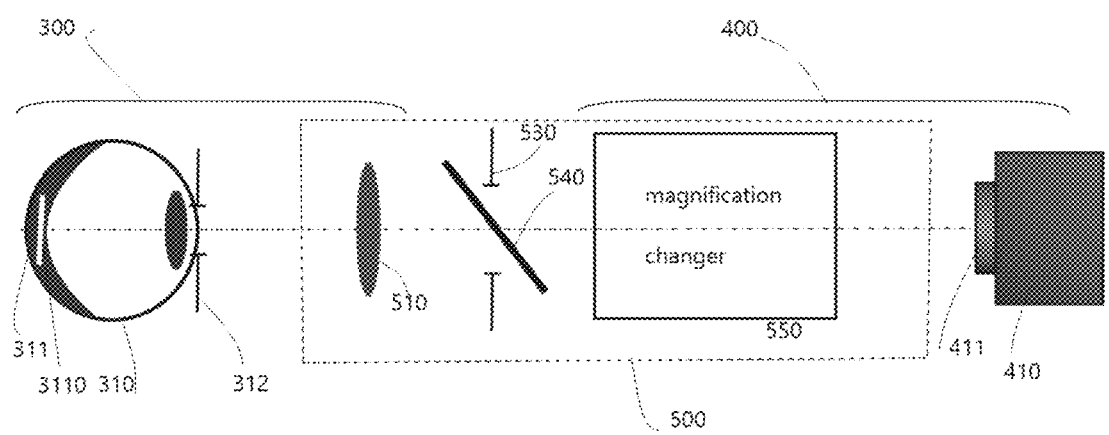
FIG. 15 is an optical configuration device with an optical magnification changer in another embodiment.

FIG. 15 is an optical configuration device 500 including an optical magnification changer 550 to vary the field of view (i.e., the slice of the retina to be imaged) 3110. By continuously zooming or changing to a new group of optical lenses to implement the optical magnification changed, the field of view 3110 varies.

Figure 16:
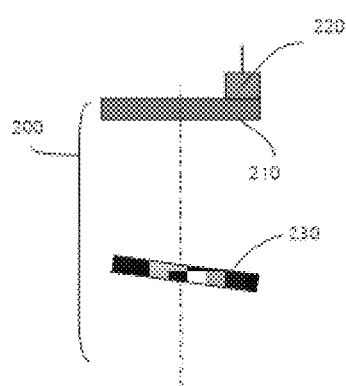
FIG. 16 is a reference arm with a removable light blocking screen inserted in another embodiment.

FIG. 16 is a reference arm 200 with removable light blocking screen 230 inserted. The light blocking screen 230 is a light absorbing plate whose axis is preferred to slightly deviate from the optical axis. The light blocking screen can also be a light reflecting plate in reference arm 200, which reflects off the light out of optical path that is absorbed by one or more absorber plates installed within the apparatus. In this case, the embodiment acts as a traditional fundus camera.

Figure 17:
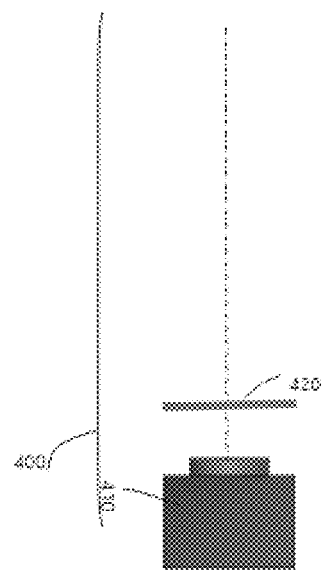
FIG. 17 is a detection arm with a light filter inserted in another embodiment.

FIG. 17 is a detection arm 400 with a light filter 420 inserted. In order to detect the back scattered and reflected light which is different from the illumination light, a specific spectrum filter can be used to filter out the illumination light to implement higher contrast. This configuration allows for the fundus imaging with the florescent light excited from the retina 311, such as fluorescein angiography (FA), fundus autofluorescence (FAF), indocyanine green angiography (ICG). Under this situation, the embodiment will lose the depth sectioning ability to work as a traditional fundus.

Figure 18:
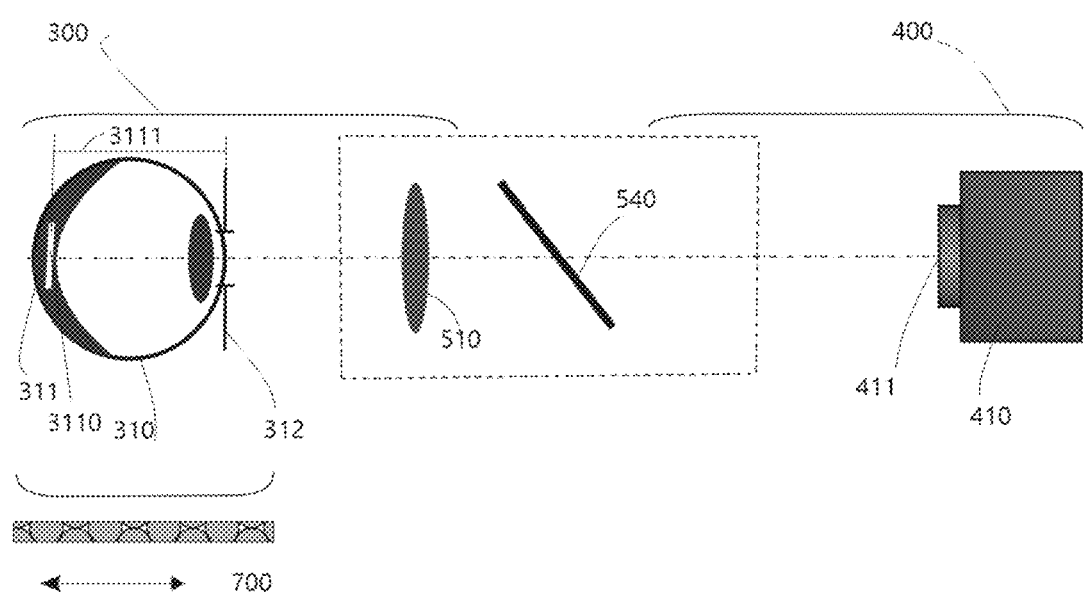
FIG. 18 is a scheme to axially displace the physical eye for scanning retina slice at different depth in another embodiment.

FIG. 18 is a scheme to axially displace the physical eye for scanning retina slice 3110 to a different depth 3111. The optical conjugation device 500 optically always conjugates the slice 3110 of the retina 311 to the sensitive surface 411 of the camera 410 in detection arm 400 at the different depth 3111, and 3D image stacks is formed. Since the thickness of the retina is within several millimeters, the subjective will not be seriously disturbed for the movement of his or her eye (i.e., the head).

The foregoing description of the present disclosure, along with its associated embodiments, has been presented for purposes of illustration only. It is not exhaustive and does not limit the present disclosure to the precise form disclosed. Those skilled in the art will appreciate from the foregoing description that modifications and variations are possible in light of the above teachings or may be acquired from practicing the disclosed embodiments.

Likewise, the steps described need not be performed in the same sequence discussed or with the same degree of separation. Various steps may be omitted, repeated, combined, or divided, as necessary to achieve the same or similar objectives or enhancements. Accordingly, the present disclosure is not limited to the above-described embodiments, but instead is defined by the appended claims in light of their full scope of equivalents.

What is claimed is:

1. An apparatus for parallel optical coherence tomographic funduscope, comprising: an illumination arm; a processing unit; and a retina imaging interferometer comprising a sample arm, a reference arm, a detection arm and a blocking unit to block unwanted back reflections from optical elements and eye, wherein the illumination arm includes a light source used for emitting incident lights; the processing unit is used for processing raw images from the retina imaging interferometer to obtain fundus images; the retina imaging interferometer is used for acquiring the raw images by a camera in the detection arm, based on (i) the interference when a reference light reflected from a reference mirror in the reference arm meets a sample light backscattered from a slice of the retina at a given depth in the sample arm and (ii) the sample light backscattered from a slice of the retina at a given depth in the sample arm; the illumination and the reference arms are located in a first light path, the sample and the detection arms are located in a second light path, wherein the first light path and the second light path have at least one intersection, and the blocking unit comprises a detection pupil located in the second light path to block unwanted back reflections from optical elements and eye, wherein the detection pupil is conjugated with eye pupil.

2. The apparatus for parallel optical coherence tomographic funduscope according to claim 1, further comprising:
a first means for axially displacing the depth of the slice of the retina to be imaged by the camera.

3. The apparatus for parallel optical coherence tomographic funduscope according to claim 1, further comprising:
a second means for varying the optical path length of the reference arm to match that of the sample arm.

4. An apparatus for parallel optical coherence tomographic funduscope according to claim 1, wherein
the processing unit is used for processing temporal variants of the raw images to present the sub-cellular motions, vibrations and metabolic intracellular activities in retina.

5. The apparatus for parallel optical coherence tomographic funduscope according to claim 1, further comprising:
a third means for modulating the relative optical path difference at scale of the wavelength between the sample and the reference arms, around the retina slice at the given depth of the retina.

6. The apparatus for parallel optical coherence tomographic funduscope according to claim 1, wherein
the illumination arm further comprises a light filter through that the light with a selected wavelength incident into the retina imaging interferometer for fundus imaging.

7. The apparatus for parallel optical coherence tomographic funduscope according to claim 1, wherein
the illumination arm further comprises a light intensity modulator to timely vary the light source power to create pulsed or temporarily continuous varying incident light.

8. The apparatus for parallel optical coherence tomographic funduscope according to claim 1, wherein
the illumination arm further comprises several light sources to be combined in the light path by a beamsplitter or dichroic filter.

9. The apparatus for parallel optical coherence tomographic funduscope according to claim 1, wherein
the light source includes LED, Xenon or halogen lamp.

10. An apparatus for parallel optical coherence tomographic funduscope according to claim 1, wherein the apparatus adopts bright field illumination or dark field illumination.

11. The apparatus for parallel optical coherence tomographic funduscope according to claim 1, wherein
the illumination arm further comprises an internal fixation target to suppress the influence of eye movement and keep the imaging field stable.

12. The apparatus for parallel optical coherence tomographic funduscope according to claim 1, further comprising:
an optical conjugation device for optically conjugating the retina to the sensitive surface of the camera, wherein
the optical conjugation device comprises a switchable trial lens to statically correct part of the eye aberrations when the corresponding eye aberrations is out of the dynamic correction range of the funduscope.

13. The apparatus for parallel optical coherence tomographic funduscope according to claim 1, further comprising:
an optical conjugation device for optically conjugating the retina to the sensitive surface of the camera, wherein
the optical conjugation device comprises a badal system.

14. The apparatus for parallel optical coherence tomographic funduscope according to claim 1, wherein
the detection arm comprises an internal fixation target for keeping the imaging field stable.

15. The apparatus for parallel optical coherence tomographic funduscope according to claim 1, wherein
the detection arm comprises several cameras to be combined in the light path by a beamsplitter or dichroic filter.

16. The apparatus for parallel optical coherence tomographic funduscope according to claim 1, wherein
the sample arm comprises a chin rest to support the head of the subject.

17. The apparatus for parallel optical coherence tomographic funduscope according to claim 1, wherein
the optical conjugation device comprises an optical magnification changer to vary the field of view.

18. The apparatus for parallel optical coherence tomographic funduscope according to claim 1, wherein
the reference arm further comprises a removable light blocking unit used to switch off depth sectioning ability of the funduscope.

19. The apparatus for parallel optical coherence tomographic funduscope according to claim 1, wherein
the detection arm further comprises a light filter through which the light with different wavelength is compared to the incident light to be received by the camera.

20. The apparatus for parallel optical coherence tomographic funduscope according to claim 1, wherein
the illumination arm further comprises an illumination pupil with fixed or adjustable shape.

* * * * *